(12) United States Patent
Hamilton et al.

(10) Patent No.: US 7,488,828 B2
(45) Date of Patent: Feb. 10, 2009

(54) PROCESS FOR THE PREPARATION OF 4-TRIFLUOROMETHYL-2(1H)-PYRIDINONE

(75) Inventors: Christopher Thomas Hamilton, Midland, MI (US); Michael Frederick Gullo, Midland, MI (US); Michael Allen Gonzalez, Sanford, MI (US); Gary Alan Roth, Midland, MI (US); David Bruce Gorman, Midland, MI (US); Joachim Gebhardt, Wachenheim (DE); Norbert Götz, Worms (DE); Hagen Jaedicke, Ludwigshafen (DE); Guido Mayer, Gönnheim (DE); Michael Rack, Heidelberg (DE)

(73) Assignee: Dow AgroSciences LLC, Indianapolis, IN (US)

( * ) Notice: Subject to any disclaimer, the term of this patent is extended or adjusted under 35 U.S.C. 154(b) by 768 days.

(21) Appl. No.: 11/166,485

(22) Filed: Jun. 24, 2005

(65) Prior Publication Data

US 2005/0288511 A1    Dec. 29, 2005

(51) Int. Cl.
*C07D 211/72* (2006.01)
(52) U.S. Cl. ...................................... 546/290; 546/303
(58) Field of Classification Search ................ 546/290, 546/303
See application file for complete search history.

(56) References Cited

U.S. PATENT DOCUMENTS 6,130,335 A    10/2000    Johnson et al.

*Primary Examiner*—Janet L. Andres
*Assistant Examiner*—Raymond Covington
(74) *Attorney, Agent, or Firm*—Craig Mixan

(57) ABSTRACT

4-Trifluoromethyl-2(1H)-pyridinone is prepared by reaction of 4-alkoxy-1,1,1-trifluorobut-3-en-2-one or 4,4-dialkoxy-1,1,1-trifluorobutan-2-one with a trialkyl phosphonoacetate followed by cyclization.

6 Claims, No Drawings

PROCESS FOR THE PREPARATION OF 4-TRIFLUOROMETHYL-2(1H)-PYRIDINONE

BACKGROUND OF THE INVENTION

The present invention concerns a process for the preparation of 4-trifluoromethyl-2(1H)-pyridinone.

U.S. Pat. No. 6,130,335 describes certain substituted pyridinesulfonamide compounds and their use as herbicides. 2-Methoxy-4-trifluoromethylpyridine is a useful intermediate for the preparation of certain of these herbicides. 2-Methoxy-4-trifluoromethylpyridine, in turn, can be conveniently prepared from 4-trifluoromethyl-2(1H)-pyridinone, for example, by chlorination with thionyl chloride followed by methoxylation using sodium methoxide. It would be advantageous to produce 4-trifluoromethyl-2(1H)-pyridinone efficiently and in high yield from a non-pyridine source.

SUMMARY OF THE INVENTION

The present invention concerns the preparation of 4-trifluoromethyl-2(1H)-pyridinone from 4-alkoxy-1,1,1-trifluorobut-3-en-2-one or 4,4-dialkoxy-1,1,1-trifluorobutan-2-one. More particularly, the present invention concerns a process for the preparation of 4-trifluoromethyl-2(1H)-pyridinone (I),

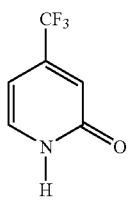

(I)

which comprises:

i) contacting either a 4-alkoxy-1,1,1-trifluorobut-3-en-2-one of the formula

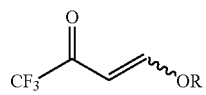

in which R represents $C_1$-$C_4$ alkyl,
or a 4,4-dialkoxy-1,1,1-trifluorobutan-2-one of the formula

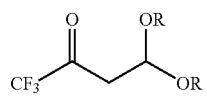

in which each R independently represents a $C_1$-$C_4$ alkyl,
with a trialkyl phosphonoacetate of the formula:

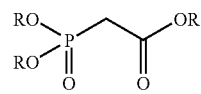

in which R is as previously defined, in the presence of a base and an alcohol or glycol solvent to provide a mixture of condensation products of the formula

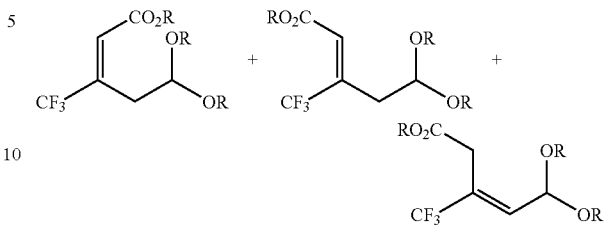

in which R is as previously defined; and ii) cyclizing the mixture of condensation products to provide 4-trifluoromethyl-2(1H)-pyridinone.

The mixture of condensation products may be cyclized to 4-trifluoromethyl-2(1H)-pyridinone by:

(a) reacting with an ammonium salt of an organic acid and/or with a mineral acid and/or with formamide.

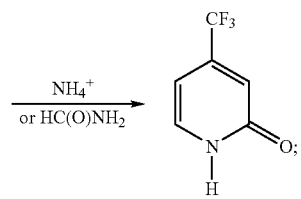

(b) reacting with an unsubstituted amide and methoxide to form a mixture of amides which is subsequently cyclized with acid

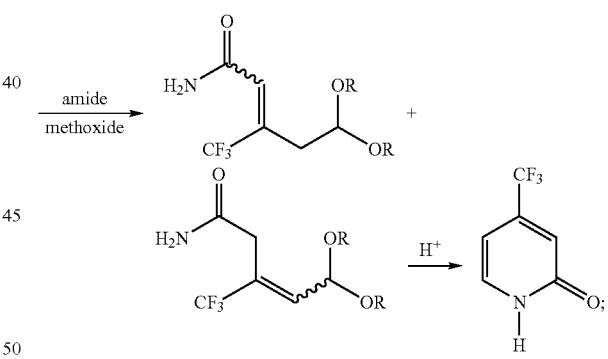

(c) reacting with an acid and water to form the lactone which is subsequently reacted with ammonia

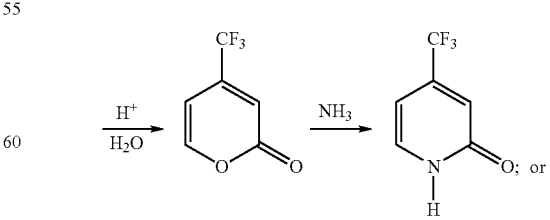

(d) reacting with an organic anhydride and pyridinium p-toluenesulfonate (PPTS) to form a mixture of dienoates which is subsequently cyclized by reacting with an ammonium salt of an organic acid (R' represents alkyl or aryl) or a mineral acid or with formamide as in (a) or by reacting with an unsubstituted amide and methoxide to form a mixture of amides which is subsequently cyclized with acid as in (b).

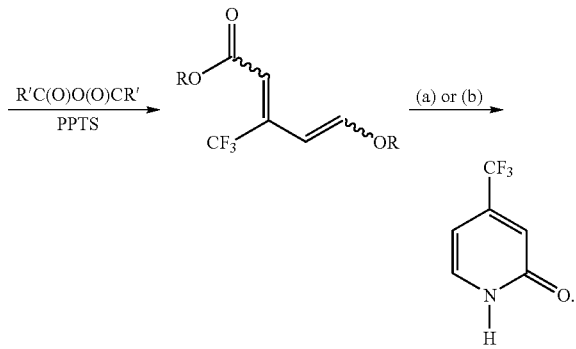

DETAILED DESCRIPTION OF THE INVENTION

4-Trifluoromethyl-2(1H)-pyridinone (I) can also be represented by its tautomer, 4-trifluoromethyl-2-pyridinol (II).

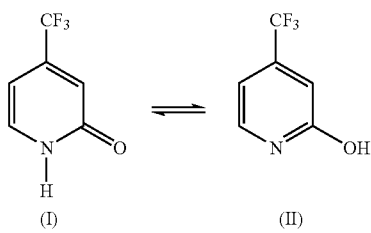

In the first step of the present invention, a 4-alkoxy-1,1,1-trifluorobut-3-en-2-one of the formula

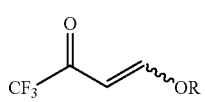

in which R represents $C_1$-$C_4$ alkyl
or a 4,4-dialkoxy-1,1,1-trifluorobutan-2-one of the formula

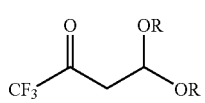

in which each R independently represents a $C_1$-$C_4$ alkyl is reacted with a trialkyl phosphonoacetate of the formula

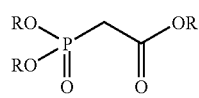

to provide a mixture of condensation products that result from reaction of 1 mole of butenone or butanone with 1 mole of phosphonoacetate, followed by loss of dialkyl phosphate and addition of 0-2 moles of alcohol. These condensation products can exist in a variety of isomeric forms. Typical of the mixture are compounds of the formula:

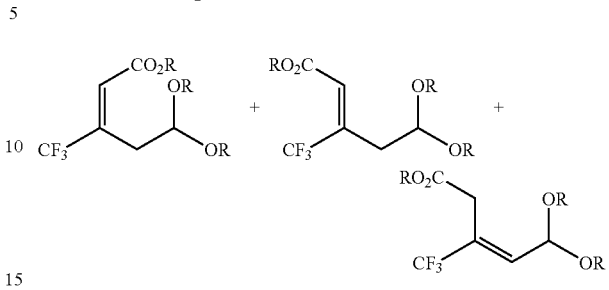

in which each R independently represents a $C_1$-$C_4$ alkyl, with $CH_3$ and $CH_2CH_3$ groups being preferred.

Approximately equimolar quantities of 4-alkoxy-1,1,1-trifluorobut-3-en-2-one or 4,4-dialkoxy-1,1,1-trifluorobutan-2-one and trialkyl phosphonoacetate are generally used in the process, although excesses of one or the other may be employed.

4-Alkoxy-1,1,1-trifluorobut-3-en-2-one may be converted to 4,4-dialkoxy-1,1,1-trifluorobutan-2-one by mixing 4-alkoxy-1,1,1-trifluorobut-3-en-2-one and an alkyl alcohol. Several catalysts may be added to promote this conversion, including, but not limited to, sodium methoxide, sodium ethoxide, lithium ethoxide, triethylamine, N,N-diisopropylamine, 4-methylmorpholine, 3-picoline, calcium oxide or potassium carbonate.

The reaction of 4,4-alkoxy-1,1,1-trifluorobutan-2-one or 4-alkoxy-1,1,1-trifluorobut-3-en-2-one with trialkyl phosphonoacetate is conducted in the presence of a $C_1$-$C_4$ alkoxide. For this conversion, it is preferred to react 4,4-dialkoxy-1,1,1-trifluorobutan-2-one with a trialkyl phosphonoacetate. A stoichiometric amount of base is required, though an excess of base, e.g., from a 10 to a 50 percent excess, may be used.

The reaction of the first step is conducted in the presence of an alcohol or glycol solvent, particularly $C_1$-$C_4$ alcohols and glycols. Preferred solvents are methanol, ethanol and ethylene glycol and the solvents are preferably anhydrous. For purposes of recovery and recycle, it is most preferable for the alkoxide base and the alcohol solvent to be derived from the same $C_1$-$C_4$ alkyl group as employed in the 4-alkoxy-1,1,1-trifluorobut-3-en-2-one starting material and the trialkyl phosphonoacetate reactant. Optionally an aromatic hydrocarbon co-solvent such as toluene may be employed.

The reaction of the first step is conducted at a temperature from about −40° C. to about 60° C. Temperatures from about −10° C. to about 30° C. are usually preferred.

The product mixture is isolated by conventional techniques such as by extraction followed by evaporation of the solvent.

In a typical reaction, the 4-alkoxy-1,1,1-trifluorobut-3-en-2-one or 4,4-dialkoxy-1,1,1-trifluorobutan-2-one is added to an alcohol solution containing a catalyst between 0-25° C. After an hour or more, the trialkyl phosphonoacetate is added. After cooling to about 0° C., the mixture is slowly treated with the appropriate amount of alkali metal alkoxide in alcohol while maintaining the temperature at about 0-10° C. After the reaction is complete, the solvent is evaporated from the reaction mixture and the residue is dissolved in an organic solvent in which the inorganic components are insoluble, such as heptane or a similar alkane, toluene or methylene chloride.

The organic phase is washed with water and the solvent removed to provide the mixture of condensation products as an oil.

In the second step of the present invention, the mixture of condensation products

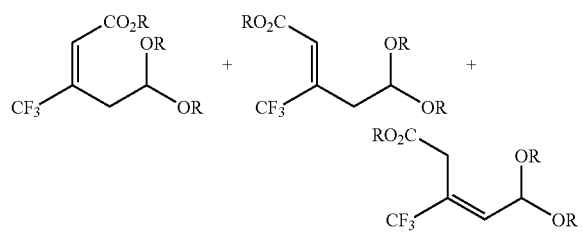

is cyclized to provide 4-trifluoromethyl-2(1H)-pyridinone.

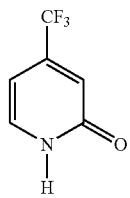

The cyclization may be accomplished by a variety of methods.

In a first method (a), the mixture of condensation products may be directly cyclized in one step to 4-trifluoromethyl-2 (1H)-pyridinone by reaction with 1) an ammonium salt of an acid, preferably an organic acid, 2) formamide, or 3) formamide with an acid or acid salt. The ammonium salt of any aliphatic or aromatic organic acid can be used, but for convenience of processing, the ammonium salts of $C_1$-$C_4$ alkanoic acids are preferred. Ammonium formate and ammonium acetate are most preferred.

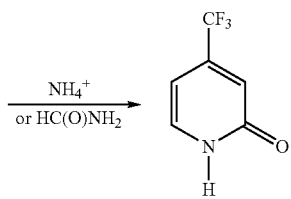

Approximately equimolar quantities of the mixture of condensation products and the ammonium salt of the organic acid are minimally required in the process, although 2-4 fold excesses of the ammonium salt of the organic acid are generally preferred.

This reaction is preferably conducted in the absence of a solvent, but a polar high-boiling solvent that is miscible with water can be used. If a solvent is used, preferred solvents include amides such as formamide, dimethyl formamide, dimethyl acetamide and 1-methyl-2-pyrrolidinone with formamide being particularly preferred.

The reaction is conducted at a temperature from about 120° C. to about 180° C. Temperatures from about 150° C. to about 160° C. are usually preferred.

The product is isolated by conventional techniques such as by precipitation followed by filtration.

In a typical reaction, the mixture of condensation products is dissolved in the polar aprotic solvent with the ammonium salt of the organic acid. The mixture is heated until the reaction is complete. After cooling to about 65° C., the mixture is diluted with water and, optionally, brine causing the product to precipitate. The 4-trifluoromethyl-2(1H)-pyridinone is isolated by filtration, washed with toluene, and dried.

In a second method (b), the mixture of condensation products may be treated with an unsubstituted amide ($RCONH_2$) and methoxide to form a mixture of amides which is subsequently cyclized with acid.

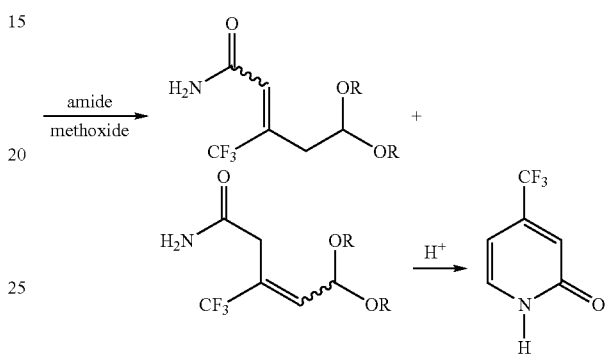

Any unsubstituted $C_1$-$C_4$ amides can be used, but formamide is preferred.

In the first step, approximately equimolar quantities of the mixture of condensation products, formamide and catalytic (e.g. 5%) methoxide (in methanol) are minimally required in the process, although an excess of formamide and 0.3-0.7 molar equivalents of methoxide (in methanol) is generally preferred.

This reaction is conveniently performed in the presence of a polar solvent that is miscible with water. Preferred solvents include amides such as formamide, dimethyl formamide, dimethyl acetamide and 1-methyl-2-pyrrolidinone, ethers such as tetrahydrofuran, and alcohols, preferably methanol.

The reaction is conducted at a temperature from about 40° C. to about 150° C. Temperatures from about 60° C. to about 100° C. are usually preferred.

The intermediate mixture of amides is cyclized without isolation by the addition of a protic inorganic or organic acid. Acetic acid and aqueous hydrochloric acid are particularly preferred. Enough acid to neutralize the base initially charged and an additional 0.05-0.20 molar equivalents is required.

In a typical reaction, the mixture of condensation products is dissolved in the polar aprotic solvent with the formamide. The alkoxide is added and the mixture is stirred at 25-40° C. temperature for 1-16 hours. The mixture is then optionally subjected to atmospheric distillation to remove volatile components. After cooling to ambient temperature, acetic acid is added and mixture is then subjected to atmospheric distillation until the pot temperature reaches about 145° C. and the overheads temperature reaches about 95° C. After cooling to ambient temperature, the 4-trifluoromethyl-2(1H)-pyridinone is isolated by standard procedures.

In a third method (c), the mixture of condensation products may be treated with a strong mineral acid and water to form a lactone which is subsequently reacted with ammonia.

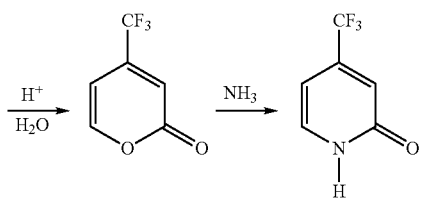

Any strong mineral acid can be used, but sulfuric acid is preferred.

In the first step, approximately equimolar quantities of the mixture of condensation products, acid and water are minimally required in the process, although an excess of water is generally preferred. This reaction is conveniently performed without any additional solvents at the reflux temperature of the mixture.

In a typical first step, the mixture of condensation products is added to water and acid and the mixture heated to reflux and distilled. The two phase distillate boiling from about 95-100° C. at atmospheric pressure is collected. The lower phase contains the intermediate lactone.

The intermediate lactone layer is then reacted with ammonia. The ammonia may be anhydrous or in solution with a solvent such as water, methanol or acetonitrile. While equimolar amounts of ammonia are minimally required, excesses are usually preferred. The reaction with ammonia is usually conducted below room temperature. With aqueous mixtures, the reaction is usually performed between about 0 and about 10° C. With anhydrous ammonia, the reaction is usually performed at about −41° C.

In a typical second step, the lactone layer is cooled to about 10° C. and vigorously stirred with additional water. Aqueous ammonia is then slowly added while maintaining the temperature below about 5° C. After warming to ambient temperature, the 4-trifluoromethyl-2(1H)-pyridinone is isolated by standard procedures.

In a fourth method (d), the mixture of condensation products may be treated with an organic anhydride and PPTS to form a mixture of dienoates which is subsequently cyclized with 1) an ammonium salt of an acid, preferably an organic acid, 2) formamide, or 3) formamide with an acid or acid salt as in method (a) or with an unsubstituted amide (RCONH$_2$) and methoxide to form a mixture of amides which is subsequently cyclized with acid as in method (b).

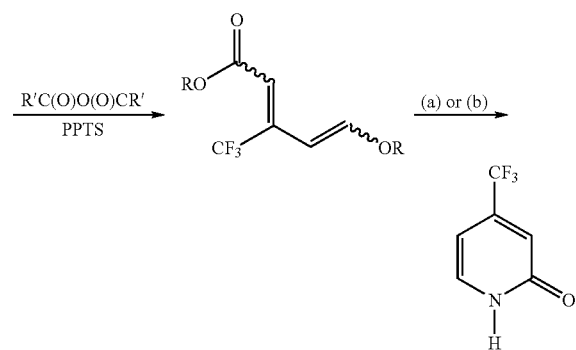

In the first step, approximately equimolar quantities of the mixture of condensation products and acetic anhydride are minimally required in the process, although an excess of acetic anhydride is generally preferred. Only a catalytic amount of PPTS is required, 1 to 2 mole percent usually being sufficient.

This reaction is conveniently performed without any additional solvents at the reflux temperature of the mixture.

In a typical first step, the mixture of condensation products, acetic anhydride and PPTS is stirred, heated to reflux and distilled at atmospheric pressure. After no more distillate is being collected and the pot temperature has reached about 145-150° C., the mixture is cooled to room temperature and the mixture of dienoates is isolated by standard procedures. The mixture of dienoates is then converted to 4-trifluoromethyl-2(1H)-pyridinone as described in the procedures of method (a) or method (b) above.

The following examples are presented to illustrate the invention.

EXAMPLES

1. Preparation of Mixture of Condensation Products

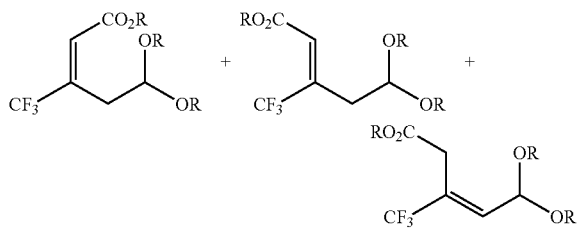

Preparation A: Conversion of 4-Ethoxy-1,1,1-trifluorobut-3-en-2-one (ETFBO) via 4-ethoxy,4-methoxy-1,1,1-trifluorobutan-2-one)

Methanol (68.5 g, 89 mL, 2.1 mol) and triethylamine (6.4 g, 9.6 mL, 0.063 mol) were combined in a nitrogen-purged 500 mL flask equipped with an addition funnel, magnetic stirring and an ice bath. ETFBO (46 g, 39.2 mL, 0.274 mol) was added to the mixture. After 1 h, the mixture was cooled to 0° C., at which point triethyl phosphonoacetate (51.0 g, 40.4 mL, 0.280 mol, 1.02 equivalent) was added in one portion. Using an addition funnel, 30% sodium methoxide in methanol (48.6 g, 50.5 mL, 14.6 g active, 0.270 mol, 0.98 equivalents) was added dropwise. The mixture exothermed to 10° C. during the 43 minute addition. After 45 minutes from completing the sodium methoxide addition, the ice bath was removed and the mixture slowly warmed to room temperature. After 2.5 h from removing the cooling bath, the mixture was concentrated by distillation (rotary evaporator), with a pot temperature of 40° C., and a reduced pressure of 40 mmHg. A total of 137.6 g of slushy concentrate remained in the pot. After distillation, the bottoms were dissolved in heptane (92 mL) and water (90 mL). The upper organic phase was removed and was concentrated by distillation (rotary evaporator) to give the mixture of products as a dark red oil (62.9 g of approximately 95% pure material).

Preparation B: Direct Conversion of ETFBO

ETFBO (10 g, 8.5 mL, 59.5 mmol) and ethanol (15 mL) were combined in a nitrogen-purged 250 mL flask equipped with an addition funnel, magnetic stirring and an ice bath. The mixture was cooled to 10° C., at which point triethyl phosphonoacetate (13.3 g, 11.8 mL, 59.5 mmol, 1 equivalent) was added in one portion. The mixture was cooled to −5° C., at which point the addition of 21% sodium ethoxide in ethanol (38.6 g, 22 mL, 8.1 g active, 119 mmol, 2 equivalents) was begun. The mixture exothermed to 3.3° C. during the 10 minute addition. The ice bath was removed upon completion of the base addition, and the mixture slowly warmed to room temperature. The mixture was stirred at room temperature overnight. GC analysis the following morning indicated adequate conversion. The mixture was concentrated by distillation (7" Vigereux column with 5" condenser), with a pot temperature of 40° C., and a reduced pressure of 120 mmHg (16.0 kilopascals). A total of 97.4 g of distillate was collected. After distillation, the bottoms were dissolved in toluene (50 mL), then washed with water (3×40 mL). An emulsion/rag layer was observed with the second wash, and both phases contained emulsions after the third wash. 20 mL saturated brine solution was added to rid the mixture of emulsions. The aqueous layer was back-extracted with 40 mL toluene. The organic phases were combined and concentrated by distillation (same column as above) to give the mixture of products as a dark red oil (26.1 g).

Identification of Components

Ethyl E-5,5-diethoxy-3-(trifluoromethyl)pent-2-enoate (1)

A sample of the condensation product isomers that had been enriched in 1 was obtained via distillation. The material was 93.7 area % 1 by GC analysis. A portion (6 g) was purified by chromatography on silica gel (30 cm×5 cm column) using 20/1 hexane/ethyl acetate. Fractions were collected and analyzed by GC. Pure fractions were combine and the solvent removed on the rotary-evaporator. The resulting clear colorless oil was dried to a constant weight (I mmHg/room temperature) to give 2.0 g of 1. The material was 99.7 area % pure by GC analysis.

$^1$H NMR (600 MHz, CDCl$_3$) δ 6.42 (br, 1H), 4.69 (t, J=5.8 Hz, 1H), 4.25 (q, J=7.2 Hz, 2H), 3.68 (dq, J=15.2, 4.8 Hz, 2H), 3.50 (dq, J=15.5, 4.7 Hz, 2H), 3.07 (d, J=5.7 Hz, 2H), 1.33 (t, J=7.0 Hz, 3H), 1.19 (t, J=7.1 Hz, 6H). GC/MS: Electron Impact (Significant Ions Observed in Decreasing Intensity (m/z)): 165, 136, 103, 193, 239, 75, 47, 238. Ammonia Chemical Ionization (Significant Ions Observed in Decreasing Intensity (m/z)): 239, 256, 302.1598(M+NH$_4$)$^+$, 210

Ethyl E-5,5-diethoxy-3-(trifluoromethyl)pent-3-enoate (2)

A sample of the condensation product isomers that had been enriched in 2 was obtained as a distillation pot bottoms. The material was 68.6 area % 2 by GC analysis. A 1.2 g sample was chromatographed on silica gel (25 cm×3.5 cm column) using 50/1 hexane/ethyl acetate. Fractions were collected and analyzed by GC. Pure fractions were combine and the solvents removed on the rotary-evaporator with final drying at 1 mmHg/room temperature. This gave 2 as a colorless liquid (0.6 g) with a purity of 99.4 area % by GC analysis. $^1$H NMR (600 MHz, CDCl$_3$) δ 6.34 (dq, J=4.8, 1.6 Hz, 1H), 5.26 (dq, J=4.8, 1.6 Hz, 1H), 4.18 (q, J=7.1 Hz, 2H), 3.64 (dq, J=15.5, 4.7 Hz, 2H), 3.55 (dq, J=15.3, 4.8 Hz, 2H), 3.38 (s, 2H), 1.27 (t, J=7.3 Hz, 3H), 1.22 (t, J=7.0 Hz, 6H). GC/MS: Electron Impact (Significant Ions Observed in Decreasing Intensity (m/z)): 165, 136, 239, 107, 67, 164, 238, 265, 39. Ammonia Chemical Ionization (Significant Ions Observed in Decreasing Intensity (m/z)): 239, 210, 256, 302.1562(M+NH$_4$)$^+$, 192.

Ethyl Z-5,5-diethoxy-3-(trifluoromethyl)pent-2-enoate (3)

A sample of the condensation product isomers that had been enriched in 3 was obtained via distillation. The material was 76.9 area % 3 via GC analysis. A 2.0 g sample was chromatographed on silica gel (21×3.5 cm column) using 20/1 hexane/ethyl acetate. Fractions were collected and analyzed by GC. Pure fractions were combined and the solvents removed on the rotary-evaporator with final drying at low pressure (1 mmHg/room temperature). This gave 3 as a clear colorless liquid (430 mg). The material was 98.2 area % pure via GC analysis.

$^1$H NMR (600 MHz, CDCl$_3$) δ 6.26 (br, 1H), 4.63 (t, J=5.6 Hz, 1H), 4.24 (q, J=7.3 Hz, 2H), 3.69 (dq, J=15.2, 4.8 Hz, 2H), 3.53 (dq, J=15.4, 4.7 Hz, 2H), 2.56 (dd, J=5.6, 1.4 Hz, 2H), 1.31 (t, J=7.3 Hz, 3H), 1.22 (t, J=6.9 Hz, 6H). GC/MS: Electron Impact (Significant Ions Observed in Decreasing Intensity (m/z)): 165, 136, 103, 193, 238, 75, 47, 211, 239. Ammonia Chemical Ionization (Significant Ions Observed in Decreasing Intensity (m/z)): 239, 302.1566(M+NH$_4$)$^+$, 256, 103, 272, 227.

2. Preparation of 4-trifluoromethyl-2(1H)-pyridinone

Method (a):

A distilled mixture of condensation products (5.0 g, 0.0176 mol)) was combined with ammonium acetate (2.7 g) and formamide (5 mL) in a flask equipped with a distillation head. The reaction was heated in an oil bath set at 155-165° C., with collection of a small amount of overhead liquids. After 2 hours, more ammonium acetate was added (0.8 g), and the mixture was heated for another 1 hour. The dark mixture was then allowed to cool to 60° C., and treated slowly with water (5 mL), with the temperature falling to 40° C. At this point, saturated aqueous sodium chloride (5 mL) was added. The resulting slurry was cooled to 15° C. over ½ hour, and then the product solids were collected by filtration and washed with a minimal amount of cold water. The resulting wet cake was analyzed by HPLC using a standard to determine a purity of 74% (66% yield).

Method (a):

The condensation product mixture (Ex. 1, 100 g, 90 g active, 0.351 moles), ammonium acetate (108.3 g, 1.40 moles, 4 equivalents), and formamide (100 mL) were combined in a nitrogen-purged 1-L flask equipped with N$_2$, magnetic stirring, a heating mantle controlled by a Variac, a thermometer, and a distillation apparatus with a 6" Vigreaux column. The mixture was heated to 155° C. After 3 hours, HPLC analysis indicated adequate conversion. The heat was removed from the flask, and when the mixture reached 65° C., water (200 mL) was added, followed by saturated brine solution (400 mL). Solids were present in the mixture at this point. The mixture was stirred at room temperature overnight. After cooling the slurry with an ice bath for 30 minutes, The solids were collected by vacuum filtration, and the wet cake washed with 100 mL water, then washed with 100 mL toluene. The solids were dried under vacuum at 60° C. to give 43.7 g of 4-trifluoromethyl-2(1H)-pyridinone as a light brown solid, which was found to be 98.1% pure by HPLC internal standard assay (0.263 moles, 74.9% isolated yield, reaction yield (based on assay of product, filtrate/water wash, and toluene wash) was 86.3%).

Method (b):

In a 50 ml flask equipped with stir bar, thermometer, short path distillation head (under nitrogen) was charged 20.1 g of condensation product, 10 ml of formamide, and 15 ml of dimethyl formamide (DMF). To the mixture was added 3.8 g of 30% sodium methoxide added (turns dark cherry red, homogeneous). After stirring at ambient temperature overnight the mixture was subjected to atmospheric distillation up to a pot temperature of 145° C. and a head temperature of 65° C. (GC/MS analysis was consistent with the formation of two isomeric amides as major components). After cooling to ambient temperature, 30 ml of acetic acid were added (mild exotherm). After stirring over night the mixture was subjected to atmospheric distillation up to a head temperature of 95° C. and a pot temperature of 145° C. The material which remained in the pot (58 g) contained 13.5 wt % 4-trifluoromethyl-2(1H)-pyridinone, corresponding to an in pot yield of 68%.

Method (c):

In a 50 ml flask equipped with stir bar, thermometer, and equipped for atmospheric distillation through a 4 inch vacuum jacketed Vigreaux column (under nitrogen) was charged the following: 18.5 g of condensation product, 22 g of water, and 1.5 g of sulfuric acid. The mixture was subjected to distillation with ~10 g collected up to 95° C. A second cut was taken in the 95-100° C. range (during which 13 additional grams of water were added). This distillate consisted of two immiscible liquids: 18.4 g of upper phase and 7.2 g of lower phase. Based on GC area % the lower layer was 90 GC area % 4-trifluoromethyl-2H-pyran-2-one, corresponding to an estimated yield of 60%. GC/MS was consistent with the desired product (m/z 164 parent), 145 (loss of F, 19), 136 (loss of CO, 28). $^1$H NMR (CDCl$_3$) δ: 7.7 (d), 6.6 d), 6.4 (dd).

In a 125 ml flask equipped with stir bar, thermometer, pressure equalizing addition funnel and under nitrogen was charged 20 g of 4-trifluoromethyl-2H-pyran-2-one distillate along with 68 g of water. After cooling the vigorously stirred mixture to ~3° C. (ice water bath), 33 g of 29 wt % NH$_4$OH was added drop wise over 20 minutes while maintaining the temperature below 5° C. (yellow solution). After stirring an additional 2 hours, 27 g of glacial acetic acid was added over 30 minutes while maintaining the temperature at 5-10° C. (yellow with solids present). After warming to 15° C., 15 g of NaCl were added. After stirring at ambient temperature the mixture was extracted with 50 ml of ethyl acetate. The extract was washed with saturated brine and concentrated to 19 g of viscous oil. The oil was determined to contain 34 wt % 4-trifluoromethyl-2(1H)-pyridinone (HPLC external standard assay), corresponding to a yield of 32%.

Method (d):

In a 50 ml round bottom flask equipped with stir bar, thermometer, and configured for atmospheric distillation through a 2" vacuum jacketed Vigreux column under nitrogen was charged 28.6 g of condensation product, 6.7 g (66 mmol) of acetic anhydride, and 0.15 g (<1 mmol) of pyridinium p-toluenesulfonate. The mixture was heated with stirring, collecting distillate at 78-90° C. Heating was stopped after no distillate was being collected and the head temp reached 135° C. After GC analysis indicated that unreacted starting material remained, another 0.8 g of acetic anhydride was added, distillation resumed until no more distillate was collected and the pot temperature reached 148° C. After cooling the homogeneous liquid was combined with 25 ml of hexanes, extracted 2×25 ml of water, then with 25 ml~10% aqueous sodium carbonate, then with 15 ml of water, dried over sodium sulfate, and then concentrated on a rotary evaporator, then under high vacuum to give 24.4 g of crude dienoate as a tea colored oil.

In a 50 ml round bottom equipped with stir bar and condenser under nitrogen was charged 10.0 g of crude dienoate, 6.0 g of ammonium acetate, and 25 ml of ethanol. After the mixture was heated at reflux (82° C.) for ~45 min, the apparatus was configured for short path distillation and ~14 g of distillate were collected at atmospheric pressure (up to ~79° C. head and ~85° C. pot temperatures). After cooling 16.6 g of formamide was added and distillation was resumed. After collecting ~8 ml of distillate at ~80° C. the mixture was allowed to cool and 1.7 g of ammonium acetate were added and distillation was continued to a pot temperature of 137° C. After cooling the heterogeneous mixture was diluted (dissolved) in ethanol to a weight of 41 g. The solution was found to contain 7.5 wt % 4-trifluoromethyl-2(1H)-pyridinone by HPLC external standard, corresponding to a 55% yield.

What is claimed is:

1. A process for the preparation of 4-trifluoromethyl-2 (1H)-pyridinone (I),

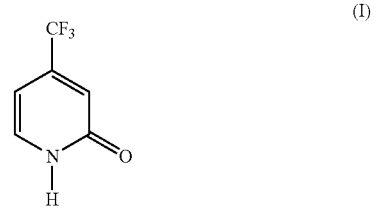

which comprises:
i) contacting either a 4-alkoxy-1,1,1-trifluorobut-3-en-2-one of the formula

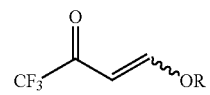

in which R represents C$_1$-C$_4$ alkyl, or a 4,4-dialkoxy-1,1,1-trifluorobutan-2-one of the formula

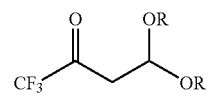

in which R is as previously defined, with a trialkyl phosphonoacetate of the formula:

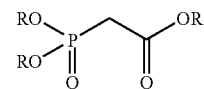

in which R is as previously defined, in the presence of a base and an alcohol or glycol solvent to provide a mixture of condensation products of the formula

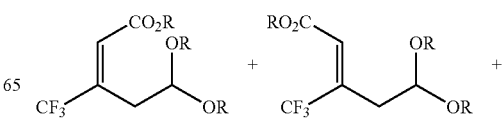

-continued

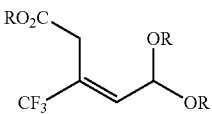

in which R is as previously defined;
and
ii) cyclizing the mixture of condensation products to provide 4-trifluoromethyl-2(1H)-pyridinone.

2. The process of claim 1 in which the mixture of condensation products is cyclized by reacting with an ammonium salt of an organic acid and/or with a mineral acid and/or with formamide.

3. The process of claim 2 in which the ammonium salt of an organic acid is ammonium formate or ammonium acetate.

4. The process of claim 1 in which the mixture of condensation products is cyclized by reacting with an unsubstituted amide and methoxide to form a mixture of amides which is subsequently cyclized with acid.

5. The process of claim 1 in which the mixture of condensation products is cyclized by reacting with an acid and water to form the lactone which is subsequently reacted with ammonia.

6. The process of claim 1 in which the mixture of condensation products is cyclized by reacting with an organic anhydride and pyridinium p-toluenesulfonate (PPTS) to form a mixture of dieneoates which is subsequently cyclized by reacting with an ammonium salt of an organic acid (R' represents alkyl or aryl) or a mineral acid or with formamide or by reacting with an unsubstituted amide and methoxide to form a mixture of amides which is subsequently cyclized with acid.

* * * * *